(12) United States Patent
Fang et al.

(10) Patent No.: US 9,610,152 B1
(45) Date of Patent: Apr. 4, 2017

(54) KIT FOR INTRODUCING A BLADDER INTO A BODY POCKET

(71) Applicants: Hsu-Wei Fang, Taipei (TW); Mark Berman, Santa Monica, CA (US)

(72) Inventors: Hsu-Wei Fang, Taipei (TW); Mark Berman, Santa Monica, CA (US)

( * ) Notice: Subject to any disclaimer, the term of this patent is extended or adjusted under 35 U.S.C. 154(b) by 14 days.

(21) Appl. No.: 14/950,084

(22) Filed: Nov. 24, 2015

(51) Int. Cl.
    *A61F 2/12*         (2006.01)
    *A61M 25/06*       (2006.01)
    *A61M 29/02*       (2006.01)
    *A61B 17/34*        (2006.01)

(52) U.S. Cl.
    CPC ............ *A61F 2/12* (2013.01); *A61B 17/3468* (2013.01); *A61M 29/02* (2013.01)

(58) Field of Classification Search
    CPC ...... A61F 2/12; A61M 25/06; A61M 25/0662; A61M 2025/0662; A61M 2025/1056; A61B 17/3421
    USPC .......................... 623/7–8; 606/108; 604/6.16
    See application file for complete search history.

(56) References Cited

U.S. PATENT DOCUMENTS

| | | | | |
|---|---|---|---|---|
| 4,341,211 A * | 7/1982 | Kline | .................. | A61M 31/007 604/514 |
| 5,507,807 A * | 4/1996 | Shippert | .................... | A61F 2/12 604/181 |
| 6,034,295 A * | 3/2000 | Rehberg | ................... | A61B 17/72 433/201.1 |
| 6,146,418 A * | 11/2000 | Berman | ..................... | A61F 2/12 623/7 |
| 7,137,995 B2 * | 11/2006 | Studin | ........................ | A61F 2/12 604/181 |
| 7,935,089 B2 * | 5/2011 | Tsao | ........................... | A61F 2/12 604/218 |
| 8,092,527 B2 * | 1/2012 | Brennan | ................... | A61F 2/12 623/8 |
| 2007/0093893 A1 * | 4/2007 | Studin | ........................ | A61F 2/12 623/8 |
| 2008/0269763 A1 * | 10/2008 | Bonde | ................ | A61B 17/3468 606/99 |
| 2009/0012356 A1 * | 1/2009 | Dann | ................... | A61B 17/0401 600/106 |
| 2011/0282195 A1 * | 11/2011 | Solar | .................. | A61M 25/0026 600/431 |
| 2013/0226296 A1 * | 8/2013 | Chernomorsky | .... | A61B 8/0841 623/8 |
| 2016/0256705 A1 * | 9/2016 | Webler, Jr. | .......... | A61B 1/00163 |
| 2016/0345970 A1 * | 12/2016 | Shanley | ............. | A61B 17/0057 |
| 2016/0346519 A1 * | 12/2016 | Bagwell | ............... | A61B 10/025 |

\* cited by examiner

*Primary Examiner* — Suzette J Gherbi
(74) *Attorney, Agent, or Firm* — Juan Carlos A Marquez; Marquez IP Law Office, PLLC

(57) ABSTRACT

A kit for introducing a bladder into a body pocket is provided. The kit comprises a holder having an interior surface, an exterior surface and at least one open end, a balloon catheter, a needle and a bladder. The holder includes a needle sheath formed on the exterior surface. The balloon catheter comprises a balloon and a tube. The needle is secured to the bladder by a suture. The bladder may be positioned in the holder with the needle received in the needle sheath. The bladder may have an inlet and an opening. Through the inlet the balloon catheter and a body prosthesis are introducible into the bladder after the bladder is placed into the body pocket, and through the opening the tube of the balloon catheter is introducible out of the bladder.

9 Claims, 5 Drawing Sheets

KIT FOR INTRODUCING A BLADDER INTO A BODY POCKET

FIELD OF THE INVENTION

The present invention pertains to a kit for introducing a bladder into a body pocket. More specifically, the invention relates to a kit for introducing a bladder such as one described in U.S. Pat. No. 6,146,418 into a body pocket.

BACKGROUND OF THE INVENTION

U.S. Pat. No. 6,146,418 (the '418 patent) discloses a body implant and method of implanting. The implant as described in the '418 patent has a separate bladder made from a bio-compatible flexible polymer into which a mobile device or prosthesis may be placed after the bladder has been introduced into a subcutaneous body pocket. By ingrowth of body tissue into pores in the bladder, the bladder may form an artificial scar with minimal spherical capsular contracture. In the current application, Applicant has developed an integral kit adapted to introduce such bladder and perform the subsequent operation.

BRIEF SUMMARY OF THE INVENTION

The present invention provides a kit for introducing a bladder into a body pocket, which comprises a holder, a balloon catheter, a bladder and a needle. The holder has an interior surface, an exterior surface and at least one open end. Further, the holder includes a needle sheath formed on the exterior surface of the holder. The balloon catheter comprises a balloon and a tube. The needle is secured to the bladder by a suture. The bladder may be positioned in the holder with the needle received in the needle sheath. The bladder has an inlet and an opening. The inlet allows the balloon catheter and a body prosthesis to be sequentially introduced into the bladder after the bladder is placed into the body pocket. In addition, after the balloon catheter is placed into the bladder, the tube of the balloon catheter may be introduced out of the bladder through the opening.

In certain embodiments of the present invention, the kit further comprises a cover. The cover is adapted to couple with the holder and the needle sheath and may be used to cover the open end and the tip of the needle when the needle is received in the needle sheath.

In one embodiment of the invention, the holder further includes a plunger configured at an opposite end of the open end. The plunger may be used to urge the bladder out of the open end and into the body pocket.

According to the present invention, the holder may include three or more, or four or more, needle sheaths formed at equal intervals surroundingly on the exterior surface of the holder. Accordingly, the kit may comprise three or more, or four or more, needles each secured to the bladder by a suture.

It is to be understood that both the foregoing general description and the following detailed description are exemplary and explanatory only and are not restrictive of the invention.

BRIEF DESCRIPTION OF THE DRAWINGS

The foregoing summary, as well as the following detailed description of the invention, will be better understood when read in conjunction with the appended drawing. In the drawings.

DETAILED DESCRIPTION OF THE INVENTION

Figure 1A:
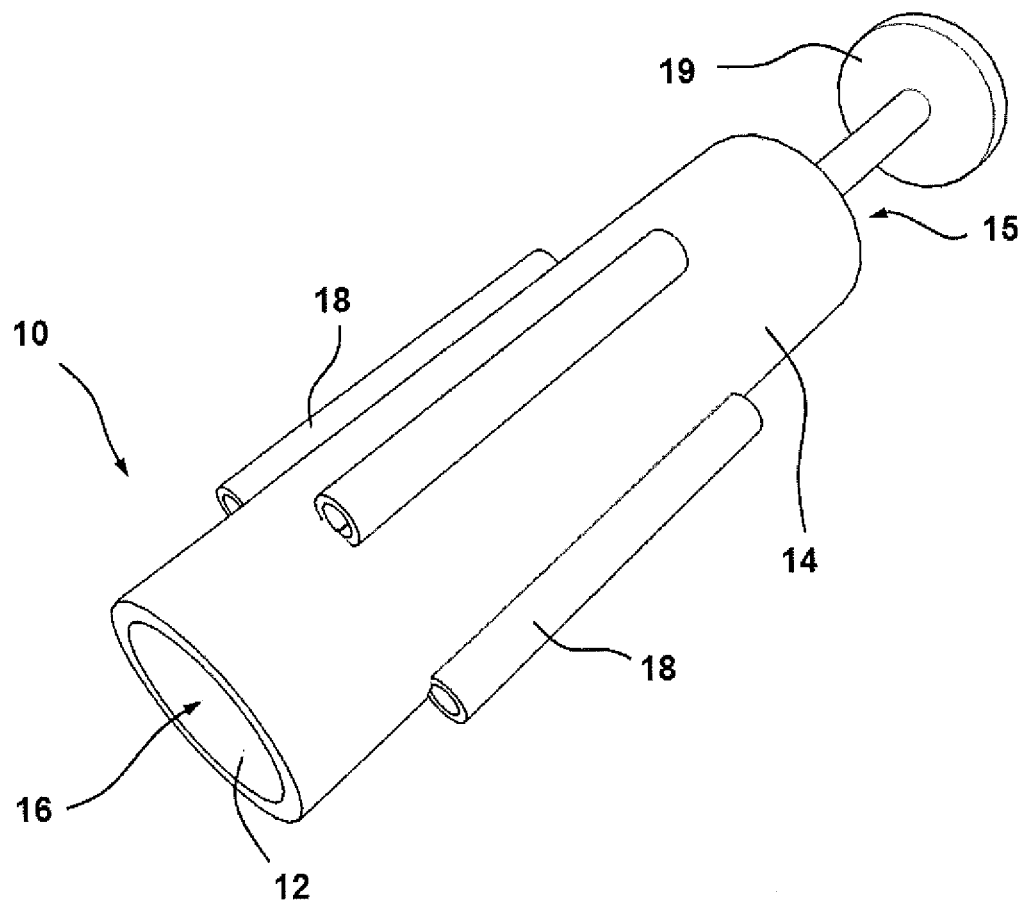
FIG. 1A is a perspective view of a holder in a kit for introducing a bladder into a body pocket in accordance with one embodiment of the present invention.
Figure 1B:
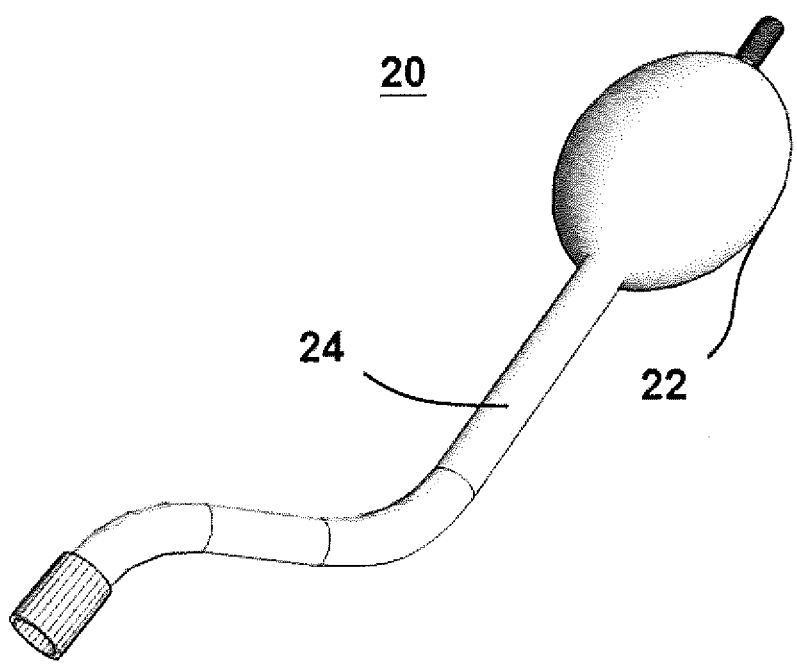
FIG. 1B is a perspective view of a balloon catheter in a kit for introducing a bladder into a body pocket in accordance with one embodiment of the present invention.
Figure 2A:
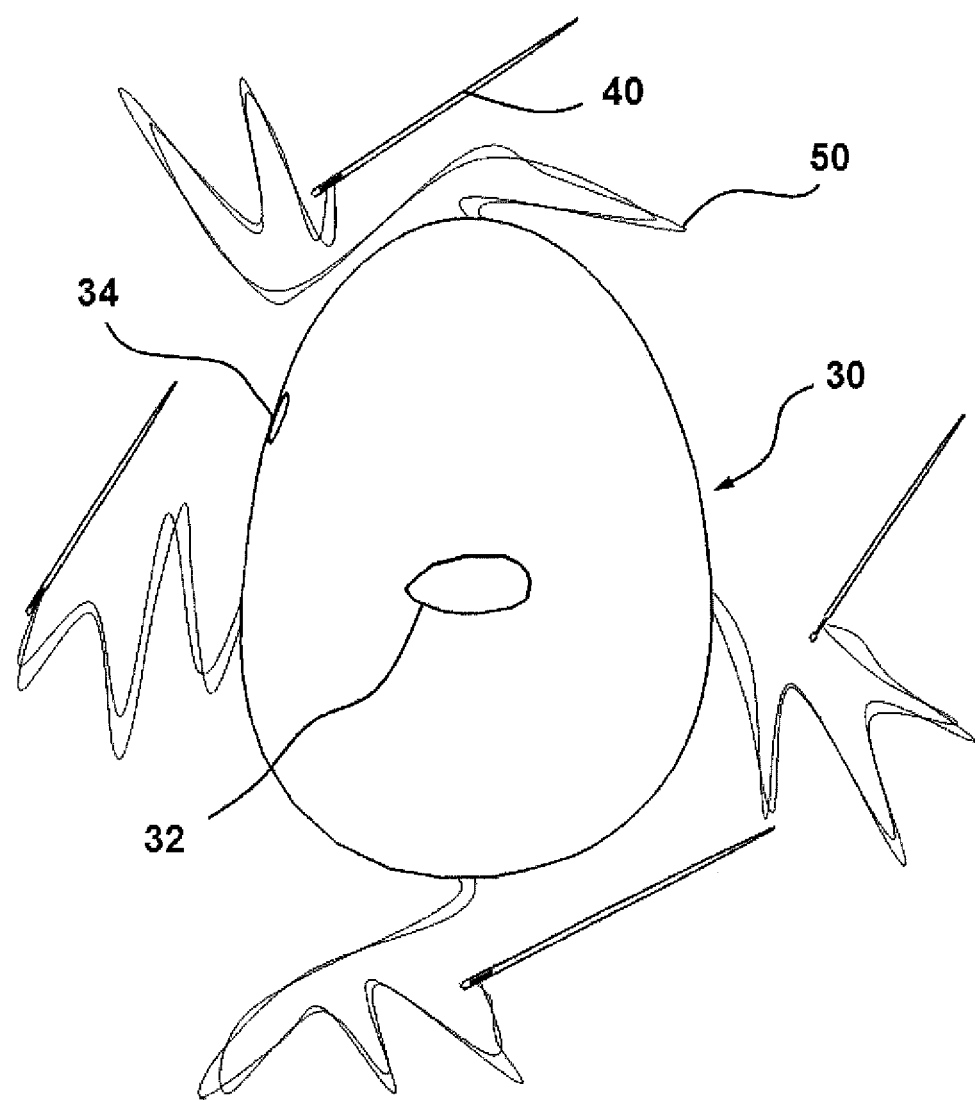
FIG. 2A is a top perspective view of a bladder in a kit for introducing a bladder into a body pocket in accordance with one embodiment of the present invention.
Figure 2B:
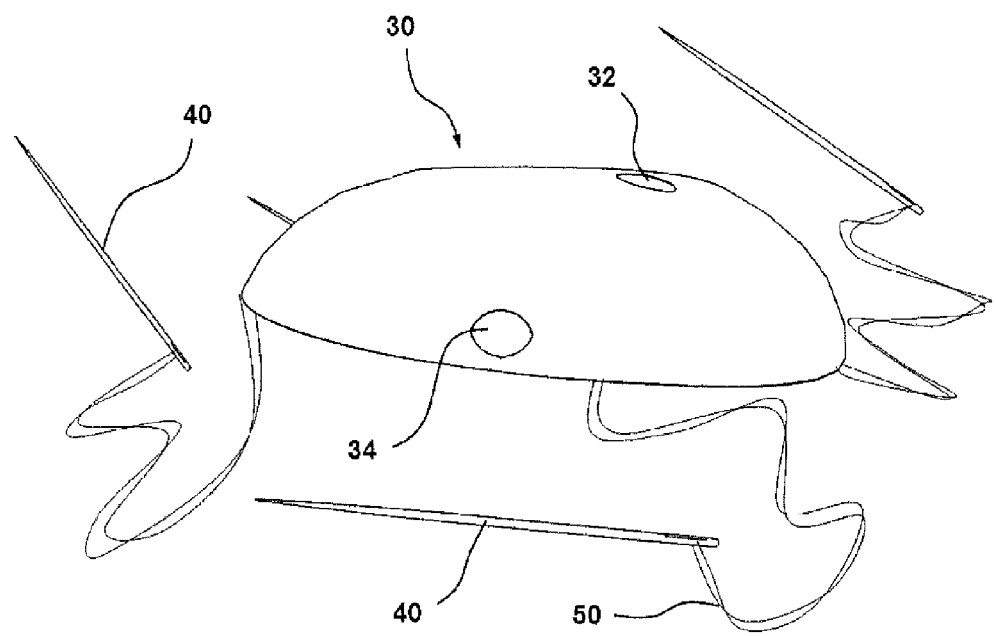
FIG. 2B is a side perspective view of a bladder in a kit for introducing a bladder into a body pocket in accordance with one embodiment of the present invention.

Referring to FIGS. 1A-2B, shown is a kit for introducing a bladder into a body pocket (not shown) according to the present invention. The kit comprises a holder 10, a balloon catheter 20, a bladder 30 and one or more needles 40. The holder 10 has an interior surface 12, an exterior surface 14, and at least one open end 16. For receiving the one or more needles 40, the holder includes one or more needle sheaths 18, respectively, formed on the exterior surface 14 of the holder 10. In addition, the holder 10 may further include a plunger 19 configured at an opposite end 15 of the open end 16. The balloon catheter 20 comprises a balloon 22 and a tube 24. The balloon catheter 20 may be a silicone rubber balloon connected to a 3-4 mm silicone rubber tube about 20 cm in length. The balloon 22, in its deflated form, is able to be withdrawn from the same incision site from which the catheter emerges. In its inflated form the balloon 22 will be able to be inflated with normal saline up to a 300 ml or 400 ml capacity with 180 ml being the most common inflation recommendation. The bladder 30 may be one according to U.S. Pat. No. 6,146,418 ('418 patent), which is hereby incorporated by reference in its entirety. The needles 40 are each secured to the bladder 30 by a suture 50 (e.g., a double strand of a non-absorbable, monofilament suture 50). The bladder 30 may be removably positioned in the holder 10 with the needles 40 received in the needle sheath 18. Further, as shown in FIG. 2, the bladder 30 has an inlet 32 and an opening 34. After the bladder 30 is placed into the body pocket (not shown), the balloon catheter 20 and a body prosthesis (e.g., a breast implant) (not shown) may be introduced into the bladder 30 through the inlet 32, as described in the '418 patent; and the opening 34 is for the introduction of the tube 24 of the balloon catheter 20 out of the bladder 30.

Preferably, the holder 10 has a generally hollow cylinder shape but is not limited thereto. The holder 10 may be made of a biocompatible material, such as a biocompatible polymer. Examples for the needles 40 include but are not limited to straight Keith needles of about three-inches in length.

To perform, for example, a breast prosthesis implant, a pocket is formed in the body of a patient, and a wound is made as an entry to the pocket. The holder 10 containing the bladder 30 and the needles 40 is positioned over the wound. Then, one by one, the needles 40 are removed from the needle sheaths 18 and passed into the pocket at an appropriate location respectively and out through the skin. Subsequently, the holder 10 is inserted to the wound from the open end 16 of the holder 10 into the pocket, and the bladder 30 is gently pushed into the pocket by the plunger 19. Of course, the bladder 30 may also be pushed into the pocket with a forceps if the holder 10 is not configured with a plunger. The sutures 50 are then pulled to further position the bladder 30, with the opening 34 aligned with the wound. Alternatively, the bladder 30 may not comprise the inlet 32 and/or the opening 34 in the first place, and the opening 34 may be generated by the operator at this stage of the operation. The sutures 50 should be temporarily secured over the right, left and inferior bolsters (not shown). Then, the balloon catheter 20 is introduced into the bladder 30 through the inlet 32 with the placement of the balloon 22 of the balloon catheter 20 in an appropriate position (e.g. most often in the superior aspect of the bladder). The tube 24 of the balloon 22 is then introduced out of the bladder 30 through the opening 34. This is generally retrieved with mosquito forceps introduced through an external skin incision and through an opening in the bladder (either prepared or created by simple puncture). The distal portion of the balloon catheter (tube part) is grasped by the forceps and withdrawn through the skin opening. A saline (with antibiotic) of 50-1,000 mL may next be added into the bladder 30. A breast implant is inserted into the bladder 30 through the inlet 32, the saline filling the bladder and pocket space is then aspirated with blunt tip suction (e.g. Yankauer device) and the suture 50 may now be clipped and removed from the bladder 30. Lastly, inflate the balloon 22 of the balloon catheter 20 through the tube 24 with sterile normal saline to stent the bladder 30 to the periphery to obtain maximum coverage of the pocket, and close the wound. The balloon catheter 20 may be removed three days to one week after the operation from the bladder through the opening 34.

Figure 3:
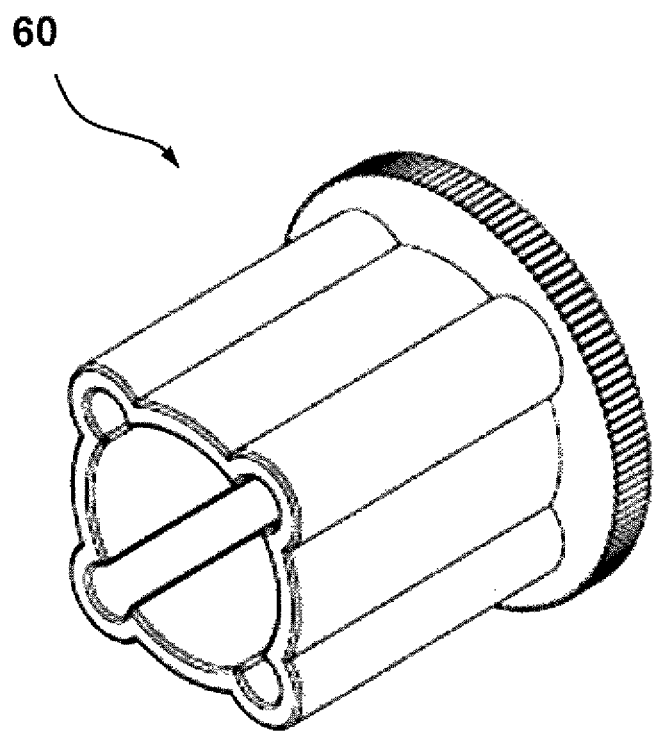
FIG. 3 is a perspective view of a cover for the holder shown in FIG. 1.

Referring to FIG. 3, a cover 60 may be further included in the kit of the present invention for safety. The cover 60 is adapted to couple with the holder 10 and the needle sheaths 18, to cover the open end 16 and the tips of the needles 40 when the needles 40 are received respectively in the needle sheaths 18.

It is believed that a person of ordinary knowledge in the art where the present invention belongs can utilize the present invention to its broadest scope based on the descriptions herein with no need of further illustration. Therefore, the descriptions as provided should be understood as of demonstrative purpose instead of limitative in any way to the scope of the present invention.

What is claimed is:

1. A kit for introducing a bladder into a body pocket comprising:
    (a) a holder having an interior surface, an exterior surface and at least one open end, the holder including a needle sheath formed on the exterior surface;
    (b) a balloon catheter comprising a balloon and a tube;
    (c) a bladder removably positioned in the holder; and
    (d) a needle secured to the bladder by a suture.

2. The kit according to claim 1, further comprising a cover adapted to couple with the holder and the needle sheath, to cover the open end and the tip of the needle when the needle is received in the needle sheath.

3. The kit according to claim 1, wherein the holder further includes a plunger configured at an opposite end of the open end.

4. The kit according to claim 1, wherein the holder includes three or more needle sheaths formed at equal intervals surroundingly on the exterior surface of the holder.

5. The kit according to claim 4 comprising three or more needles each secured to the bladder by a suture.

6. The kit according to claim 1, wherein the holder includes four or more needle sheaths formed at equal intervals surroundingly on the exterior surface of the holder.

7. The kit according to claim 6 comprising four or more needles each secured to the bladder by a suture.

8. The kit according to claim 1, wherein the bladder has an inlet through which the balloon catheter and a body prosthesis are introducible into the bladder after the bladder is placed into the body pocket.

9. The kit according to claim 1, wherein the bladder further comprise an opening through which the tube of the balloon catheter is introducible out of the bladder.

* * * * *